United States Patent [19]

Abrams et al.

[11] Patent Number: 5,013,824

[45] Date of Patent: May 7, 1991

[54] HUMAN INTERLEUKIN-4 PEPTIDES AND CONJUGATES THEREOF

[75] Inventors: John S. Abrams, Belmont; Takashi Yokota, Palo Alto; Frank Lee, Palo Alto; Ken-ichi Arai, Palo Alto, all of Calif.

[73] Assignee: Schering Corporation, Kenilworth, N.J.

[21] Appl. No.: 909,520

[22] Filed: Sep. 19, 1986

Related U.S. Application Data

[63] Continuation-in-part of Ser. No. 881,553, Jul. 3, 1986, abandoned, which is a continuation-in-part of Ser. No. 843,958, Mar. 25, 1986, which is a continuation-in-part of Ser. No. 799,668, Nov. 19, 1985, abandoned.

[51] Int. Cl.$^5$ ............... C07K 13/00; A61K 39/00; A61K 45/02
[52] U.S. Cl. .................... 530/300; 530/324; 530/326; 530/327; 530/328; 530/329; 530/351; 514/2; 424/85.1; 424/85.2
[58] Field of Search ............ 514/2, 12, 13, 14; 530/300, 324, 325, 326, 807, 829, 327, 328, 329; 424/85.1, 85.2

[56] References Cited

U.S. PATENT DOCUMENTS 4,311,639  1/1982  Ganfield et al. .
4,474,754  10/1984  Shimizu et al. .

FOREIGN PATENT DOCUMENTS

87/04723  3/1987  PCT Int'l Appl. .

OTHER PUBLICATIONS

Maizel et al., PCT WO 87/04723.
Berzofsky, *Science*, vol. 229, pp. 932–940 (1985).
Novotny et al., *Proc. Natl. Acad. Sci.*, vol. 83, pp. 226–230 (1986).
Westhof et al., *Nature*, vol. 371, pp. 123–125 (1984).
Fraga, *Can. J. Chem.*, vol. 60, pp. 2606–2610 (1982).
Marx, *Science*, vol. 226, pp. 819–821 (1984).
Roitsch et al., *Immunol. Meth.*, vol. 3, pp. 85–109 (1985).
ATCC, *ATCC Catalogue of Cell Lines & Hybridomas* (5th Ed., 1985), p. 228.
Lerner et al., *Proc. Natl. Acad. Sci.*, vol. 78, pp. 3404–3407 (1981).
Hopp et al., *Proc. Natl. Acad. Sci.*, vol. 78, pp. 3824–3828 (1981).
Sharma et al., *Science*, vol. 235, pp. 1489–1492 (1987).
Yokota et al., *Proc. Nat. Acad. Sci.*, vol. 83, pp. 5894–5898 (1986).
Walter et al., *Genetic Engineering*, vol. 5, pp. 61–91 (1983).
Palfreyman et al., *J. Immunol. Meth.*, vol. 75, pp. 383–393 (1984).
Thompson et al. (1985) *J. Immunology*, 134: 369–474.
Mehta et al. (1985), *J. Immunology*, 135: 3298–1302.
O'Hara et al. (1985), *J. Immunology*, 135: 2518–23.
Farrar et al. (1983), *J. Immunology* 131: 1838–42.
Rabin et al. (1985), PNAS, 82: 2935–39.
Hopp et al. (1981), PNAS, 78: 3824–28.

*Primary Examiner*—Richard A. Schwartz
*Assistant Examiner*—Joan Ellis
*Attorney, Agent, or Firm*—Stephen C. Macevicz

[57] ABSTRACT

Peptides derived from human interleukin-4 are provided comprising from 6 to 40 amino acids. Conjugates of the peptides and carriers are also provided for the production of polyclonal and/or monoclonal antisera to human interleukin-4.

6 Claims, 3 Drawing Sheets

```
                            Hydrophilicity

HUMAN INTERLEUKIN-4 PEPTIDES AND CONJUGATES THEREOF

CROSS REFERENCE TO RELATED APPLICATIONS

This is a continuation-in-part of copending U.S. patent application Ser. No. 881,553 filed Jul. 3, 1986 now abandoned; which is a continuation-in-part of copending application Ser. No. 843,958 filed Mar. 25, 1986; which is a continuation-in-part of copending application Ser. No. 799,668 filed Nov. 19, 1985, now abandoned; all of said copending applications being incorporated herein by reference.

BACKGROUND OF THE INVENTION

The present invention relates generally to peptides useful in the production of polyclonal and/or monoclonal antibodies, and more particularly, to peptides derived from the human lymphokine, interleukin-4 (IL-4).

For some time, it has been known that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes and other cells, immunologists now generally hold the opinion that soluble proteins (e.g., the so-called "lymphokines" or "monokines") play a critical role in controlling these cellular interactions. Thus, there is considerable interest in the isolation, characterization, and mechanisms of action of cell modulatory factors, an understanding of which should yield significant breakthroughs in the diagnosis and therapy of numerous disease states.

Lymphokines apparently mediate cellular activities in a variety of ways. They have been shown to support the proliferation, growth and differentiation of the pluripotential hematopoietic stem cells into the vast number of progenitors composing the diverse cellular lineages responsible for the immune response. These lineages often respond in a different manner when lymphokines are used in conjunction with other agents.

Cell lineages that are especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and some of the other cells (including other T-cells) making up the immune network.

Another important cell lineage is the mast cell (which has not been positively identified in all mammalian species)—a granule-containing connective tissue cell located proximal to capillaries throughout the body, with especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases the mediators (e.g., histamine, serotonin, heparin, prostaglandins, etc.) which cause allergic reactions, e.g., anaphylaxis.

Research to better understand (and thus potentially treat therapeutically) various immune disorders has been hampered by the general inability to maintain cells of the immune system in vitro. Immunologists have discovered that culturing these cells can be accomplished through the use of T-cell and other cell supernatants, which contain various growth factors, such as some of the lymphokines.

The detection, isolation and purification of these factors is extremely difficult, being frequently complicated by the complexity of the supernatants they are typically located in, the divergencies and cross-overs of activities of the various components in the mixture, the sensitivity (or lack thereof) of the assays utilized to ascertain the factors' properties, the frequent similarity in the range of molecular weights and other characteristics of the factors, and the very low concentration of the factors in their natural setting.

As more lymphokines become available, primarily through molecular cloning, interest has heightened in finding clinical applications for them. Because of physiological similarities to hormones (e.g., soluble factors, growth mediators, action via cell receptors), potential uses of lymphokines have been analogized to the current uses of hormones, e.g. Dexter, Nature, Vol. 321, pg. 198 (1986). One hope is that the levels of lymphokines in a patient can be manipulated directly or indirectly to bring about a beneficial immune response, e.g. suppression in the case of inflammation, allergy, or tissue rejection, or stimulation or potentiation in the case of infection or malignant growth. Other potential clinical uses of lymphokines include maintaining and expanding in vitro populations of certain immune system cells of one person for eventual reintroduction into the same or another person for a beneficial effect. For example, investigations are currently underway to determine whether populations of lymphokine-activated killer T cells of a patient can be expanded outside his or her body then reinjected to bring about an enhanced antitumor response. Another potential clinical use of lymphokines, particularly colony stimulating factors, such as granulocyte-macrophage colony stimulating factor (GM-CSF), and factors which enhance their activities, is stimulating blood cell generation, for example, in pre- or post-chemotherapy or radiation therapy against tumors, in treatment of myeloid hypoplasias, or in treatment of neutrophil deficiency syndromes, Dexter, Nature, Vol. 321, pg. 198 (1986). Another area where such factors would be useful is in bone marrow transplant therapy, which is being used increasingly to treat aplastic anemia and certain leukemias.

There are two properties of lymphokines that have important consequences for such clinical applications: Individual lymphokines are frequently pleiotropic. And the biological effects of one lymphokine can usually be modulated by at least one other lymphokine, either by inhibition or by potentiation. For example, tumor necrosis factor, which synergizes with gamma-interferon, stimulates interleukin-1 (IL-1) production and can activate the phagocytic activity of neutrophils. IL-1, a protein produced by activated macrophages, mediates a wide range of biological activities, including stimulation of thymocyte proliferation via induction of interleukin-2 (IL-2) release, stimulation of B-lymphocyte maturation and proliferation, fibroblast growth factor activity and induction of acute-phase protein synthesis by hepatocytes. IL-1 has also been reported to stimulate prostaglandin and collagenase release from synovial cells, and to be identical to endogenous pyrogen, Krampschmidt, *J. Leuk. Biol.*, Vol. 36, pgs. 341-355 (1984).

Interleukin-2, formerly referred to as T-cell growth factor is a lymphokine which is produced by lectin-or antigen-activated T cells. The reported biological activities of IL-2 include stimulation of the long-term in vitro growth of activated T-cell clones, enhancement of thymocyte mitogenesis, and induction of cytotoxic T-cell reactivity and plaque-forming cell responses in cultures of nude mouse spleen cells. In addition, like interferons (IFNs), IL-2 has been shown to augment natural killer cell activity, suggesting a potential use in the treatment of neoplastic diseases, Henney et al., *Nature*, Vol, 291, pgs. 335-338 (1981). Some success has been reported in such therapy, e.g. Lotze and Rosenberg, "Treatment of Tumor Patients with Purified Human Interleukin-2," pgs. 711-719, in Sorg et al., Eds. *Cellular and Molecular Biology of Lymphokines* (Academic Press, Inc., New York, 1985); and Rosenberg and Lotze, "Cancer Immunotherapy Using Interleukin-2 and Interleukin-2 Activated Lymphocytes," *Ann. Rev. Immunol.*, Vol. 4, pgs. 681-709 (1986). However, IL-2 toxicity has limited the dosages which can be delivered to cancer patients for taking advantage of these properties, Lotze and Rosenberg, pgs. 711-719; and Welte et al., pgs. 755-759, in Sorg et al. Eds. (cited above).

Recently a new human lymphokine, designated interleukin-4 (IL-4), has been cloned and characterized, Lee et al., U.S. patent application Ser. No. 799,668 filed Nov. 19, 1985; Lee et al., U.S. patent application Ser. No. 881,553 filed 3 Jul. 1986; Yokota et al., *Proc. Natl. Acad. Sci.*, Vol. 83, pgs. 5894-5898 (1986) and IL-4 is a highly pleiotropic lymphokine which exhibits activities including T cell growth factor (TCGF) activity, B cell growth factor (BCGF) activity, interleukin-2 TCGF potentiating activity, potentiation of granulocyte and macrophage colony stimulating factor (GM-CSF) stimulated granulocyte colony formation, and IgE and IgG$_1$ induction activity. These activities suggest several possible therapeutic uses, e.g. as a potentiating agent for IL-2 anticancer therapy, as a potentiating agent for GM-CSF stimulated bone marrow regeneration, or as an agent to treat bare lymphocyte syndrome. Touraine, *Lancet*, pgs. 319-321 (Feb. 7, 1981); Touraine and Bethel. *Human Immunology*, Vol. 2, pgs. 147-153 (1981); and Sullivan et al., *J. Clin. Invest.*, Vol. 76, pgs. 75-79 (1985).

An important aspect of any therapy involving drugs is the ability to predict and/or monitor concentration levels in the blood. Monoclonal antibodies are widely used for this purpose, e.g. Springer, ed., *Hybridoma Technology in the Biosciences and Medicine* (Plenum Press, N.Y., 1985); and U.S. Pat. Nos. 4,562,003; 4,486,530; and 4,255,329.

In the production of genetically engineered proteins such as IL-4, separation of the expressed protein from the transformed host cells and/or their culture supernatants is a major problem. Frequently separation procedures involve one or more passes of crude material through immunoadsorbent columns. Monoclonal antibodies specific for the protein to be purified are crucial elements of such columns. Also, such monoclonal antibodies can be used to measure the degree of purification by immunoprecipitation of elechophoretically separated proteins, or by "Western" blot analysis, e.g. Burnette, *Anal. Biochem.*, Vol. 112, pgs. 195-203 (1981).

From the foregoing it is evident that the availability of monoclonal and/or polyclonal antibodies specific for IL-4 could facilitate medical and veterinary applications of the compound by improving current methods of purification, and by providing means for monitoring concentrations of IL-4 in body fluids, such as blood, urine, or the like.

SUMMARY OF THE INVENTION

The present invention includes peptides derived from human IL-4, and immunogens comprising conjugates between carriers and peptides of the invention. The term immunogen as used herein refers to a substance which is capable of causing an immune response. The term carrier as used herein refers to any substance which when chemically conjugated to a peptide of the invention permits a host organism immunized with the resulting conjugate to generate antibodies specific for the conjugated peptide. Carriers include red blood cells, bacteriophages, proteins, or synthetic particles such as agarose beads. Preferably carriers are proteins, such as serum albumin, gamma-globulin, keyhole limpet hemocyanin, thyroglobulin, ovalbumin, fibrinogen, or the like.

Peptides of the invention are defined in terms of their positions within the amino acid sequence of the native human IL-4 polypeptide defined by Formula I.

Formula I

His—Lys—Cys—Asp—Ile—Thr—Leu—Gln—Glu—Ile—
Ile—Lys—Thr—Leu—Asn—Ser—Leu—Thr—Glu—Gln—
Lys—Thr—Leu—Cys—Thr—Glu—Leu—Thr—Val—Thr—
Asp—Ile—Phe—Ala—Ala—Ser—Lys—Asn—Thr—Thr—
Glu—Lys—Glu—Thr—Phe—Cys—Arg—Ala—Ala—Thr—
Val—Leu—Arg—Gln—Phe—Tyr—Ser—His—His—Glu—
Lys—Asp—Thr—Arg—Cys—Leu—Gly—Ala—Thr—Ala—
Gln—Gln—Phe—His—Arg—His—Lys—Gln—Leu—Ile—
Arg—Phe—Leu—Lys—Arg—Leu—Asp—Arg—Asn—Leu—
Trp—Gly—Leu—Ala—Gly—Leu—Asn—Ser—Cys—Pro—
Val—Lys—Glu—Ala—Asn—Gln—Ser—Thr—Leu—Glu—
Asn—Phe—Leu—Glu—Arg—Leu—Lys—Thr—Ile—Met—
Arg—Glu—Lys—Tyr—Ser—Lys—Cys—Ser—Ser

Amino acids of Formula I are numbered with respect to the N-terminus of the native IL-4 polypeptide. Thus, $Ser_{107}$ is serine at position 107. Peptides are defined as fragments of the native IL-4 polypeptide. Thus, the peptide designated herein by $Tyr_{56}$—$Glu_{60}$ is equivalent to the peptide Tyr—Ser—His—His—Glu. Groups of peptides of the invention are also defined in terms of fragments of the native IL-4 polypeptides. Thus, the group designated herein as $[Tyr_{56}$—$Glu_{60}]_{3-5}$ consists of all 3-5 amino acid peptides (i.e. all 3-mers, 4-mers, and 5-mers) whose sequences are identical to all or part of the peptide $Tyr_{56}$—$Glu_{60}$. That is, the group consists of the following six peptides: Tyr—Ser—His—His—Glu, Tyr—Ser—His—His, Ser—His—His—Glu, Tyr—Ser—His, Ser—His—His, and His—His—Glu; or equivalently YSHHE, YSHH, SHHE, YSH, SHH, and HHE.

Generally the invention includes all 6-mer to 40-mer peptide fragments of native human IL-4, i.e. [His$_1$—Ser$_{129}$]$_{6-40}$. Preferably, the invention includes 6-mer to 40-mer peptide fragments which include the N-terminal or C-terminal sequences of the native human IL-4 polypeptide, or which correspond to sequences of the native human IL-4 polypeptide that have relatively high average hydrophilicity, as determined by Hopp-Woods or related analysis, e.g. Hopp and Woods, *Proc. Natl. Acad. Sci.*, Vol. 78, pgs. 3824–3828 (1981); or Kyte and Doolittle, *J. Mol. Biol.*, Vol. 157, pgs. 105–132 (1982). As explained more fully below, FIG. 1 illustrates the results of a Hopp-Woods analysis of the native human IL-4 polypeptide. In particular, the latter set of preferred peptides of the invention includes the following groups: [His$_1$—Thr$_{31}$]$_{6-31}$, [Glu$_{26}$—Arg$_{53}$]$_{6-28}$, [Ala$_{48}$—Trp$_{91}$]$_{6-40}$, and [Leu$_{86}$—Ser$_{129}$]$_{6-40}$. More preferably, the above groups include [His$_1$—Thr$_{25}$]$_{6-25}$, [Ala$_{35}$—Arg$_{47}$]$_{6-13}$, [His$_{59}$—Leu$_{90}$]$_{6-32}$, and [Pro$_{100}$—Ser$_{129}$]$_{6-29}$.

Standard symbols are used throughout for amino acids, e.g. Cohen, "Nomenclature and Symbolism of alpha-Amino Acids," *Methods in Enzymology*, Vol. 106, pgs. 3–17 (Academic Press, N.Y., 1984). Accordingly, Table I of this reference is incorporated by reference.

BRIEF DESCRIPTION OF THE DRAWINGS

FIG. 1 is a bar graph presenting the hydrophilicity of the amino acids of the native human IL-4 polypeptide.

DETAILED DESCRIPTION OF THE INVENTION

The invention includes peptides derived from native human IL-4 which are capable of eliciting an antibody response when conjugated to a carrier. The invention also includes the peptide-carrier conjugates themselves.

Peptides of the invention may also have utility as agonists and/or antagonists of human IL-4. Human IL-4 is highly pleiotropic; it has been shown to exhibit T-cell growth factor (TCGF) activity, B cell growth factor activity, major histocompatibility complex antigen induction activity, IgG$_1$ and IgE induction activity, and interleukin-2 TCGF enhancing activity, to name a few, e.g. Yokota et al. (cited above). Some of these activities may be related to clinical utilities and/or unwanted side effects. Some peptides of the present invention may serve as antagonists of specific IL-4 side effects, or agonists of specifically desired effects.

Peptides of the invention are synthesized by standard techniques, e.g. Stewart and Young, *Solid Phase Peptide Synthesis*, 2nd Ed. (Pierce Chemical Company, Rockford, Ill., 1984). Preferably a commercial automated synthesizer is used, e.g. Vega Biochemicals (Tucson, Ariz.) models 296A or B, or Applied Biosystems, Inc. (Foster City, Calif.) model 430A.

Peptides of the invention are assembled by solid phase synthesis on a cross-linked polystyrene support starting from the carboxyl terminal residue and adding amino acids in a stepwise fashion until the entire 34 residue chain had been formed. The synthesis was performed on a fully automated peptide synthesizer (Applied Biosystems, Inc. model 430A). The following references are guides to the chemistry employed during synthesis: Merrifield, J. Amer. Chem. Soc., Vol. 85, pg. 2149 (1963); Kent et al., pg 185, in *Peptides* 1984, Ragnarsson, Ed. (Almquist and Weksell, Stockholm, 1984); Kent et al., pg. 217 in *Peptide Chemistry* 84, Izumiya, Ed. (Protein Research Foundation, B. H. Osaka, 1985); Merrifield, Science, Vol. 232, pgs. 341–347 (1986); and references cited in this latter reference.

In solid state synthesis it is most important to eliminate synthesis by-products, which are primarily termination, deletion, or modification peptides. Most side reactions can be eliminated or minimized by use of clean, well characterized resins, clean amino acid derivatives, clean solvents, and the selection of proper coupling and cleavage methods and reaction conditions, e.g. Barany and Merrifield, *The Peptides*, Cross and Meienhofer, Eds., Vol. 2, pgs 1–284 (Academic Press, New York, 1979). It is important to monitor coupling reactions to determine that they proceed to completion so that deletion peptides missing one or more residues will be avoided. The quantitative ninhydrin reaction is useful for that purpose, Sarin et al. Anal. Biochem, Vol. 117, pg 147 (1981). jNα-t-butyloxycarbonyl (t-Boc)-amino acids were used with appropriate side chain protecting groups stable to the conditions of chain assembly but labile to strong acids. After assembly of the protected peptide chain, the protecting groups were removed and the peptide anchoring bond was cleaved by the use of low then high concentrations of anhydrous hydrogen fluoride in the presence of a thioester scavenger, Tam et al., J. Amer. Chem. Soc., Vol. 105, pg. 6442 (1983).

Side chain protecting groups used were Asp(OBzl), Glu(OBzl), Ser(Bzl), Thr(Bzl), Lys(Cl-Z), Tyr(Br-Z), Arg(N$^G$Tos), Cys(4-MeBzl), and His(ImDNP). (Bzl, benzyl; Tos toluene sulfoxyl; DNP, dinitrophenyl; Im, imidazole; Z, benzyloxgycarbonyl. The remaining amino acids had no side chain protecting groups. All the amino acids were obtained from Peninsula Laboratories, except the tBoc-His(ImDNP), which was from Chemical Dynamics and was crystallized from ethanol before use. For each cycle the tBoc Nα protected peptide-resin was exposed to 65 percent trifluoroacetic acid (from Eastman Kodak) (distilled before use) in dichloromethane (DCM), (Mallenckrodt): first for 1 minute then for 13 minutes to remove the Nα-protecting group. The peptide-resin was washed in DCM, neutralized twice with 10 percent diisopropylethylamine (DIEA) (Aldrich) in dimethylformamide (DMF) (Applied Biosystems), for 1 minute each. Neutralization was followed by washing with DMF. Coupling was performed with the preformed symmetric anhydride of the amino acid in DMF for 16 minutes. The preformed symmetric anhydride was prepared on the synthesizer by dissolving 2 mmol of amino acid in 6 ml of DCM and adding 1 mmol of dicyclohexycarbodiimide (Aldrich) in 2 ml of DCM. After 5 minutes, the activated amino acid was transferred to a separate vessel and the DCM was evaporated by purging with a continuous stream of nitrogen gas. The DCM was replaced by DMF (6 ml total) at various stages during the purging. After the first coupling, the peptide-resin was washed with DCM, 10 percent DIEA in DCM, and then with DCM. For recoupling, the same amino acid and the activating agent, dicyclohexylcarbodiimide, were transferred sequentially to the reaction vessel. After activation in situ and coupling for 10 minutes, sufficient DMF was added to make a 50 percent DMF-DCM mixture, and the coupling was continued for 15 minutes. Arginine was coupled as a preformed hydroxybenzotriazole (Aldrich) ester in DMF for 60 minutes and then recoupled in the same manner as the other amino acids. Asparagine and glutamine were coupled twice as preformed hydroxybenzotriazole esters in DMF, 40 minutes for each coupling. For all residues, the resin was washed after the second coupling and a sample was automatically taken for monitoring residual uncoupled α-amine by quantitative ninhydrin reaction, Sarin et al. (cited above).

The general technique of linking synthetic peptides to a carrier is described in several references, e.g. Walter and Doolittle, "Antibodies Against Synthetic Peptides," in Setlow et al., eds., *Genetic Engineering*, Vol. 5, pgs. 61–91 (Plenum Press, N.Y., 1983); Green et al. *Cell*, Vol. 28, pgs. 477–487 (1982); Lerner et al., *Proc. Natl. Acad. Sci.*, Vol. 78, pgs. 3403–3407 (1981); Shimizu et al., U.S. Pat. No. 4,474,754; and Ganfield et al., U.S. Pat. No. 4,311,639. Accordingly, these references are incorporated by reference. Also, techniques employed to link haptens to carriers are essentially the same as the above-referenced techniques, e.g. chapter 20 in Tijsseu *Practice and Theory of Enzyme Immunoassays* (Elsevier, N.Y., 1985).

The four most commonly used schemes for attaching a peptide to a carrier are (1) glutaraldehyde for amino coupling, e.g. as disclosed by Kagan and Glick, in Jaffe and Behrman, eds. *Methods of Hormone Radioimmunoassay*, pgs. 328–329 (Academic Press, N.Y., 1979), and Walter et al. *Proc. Natl. Acad. Sci.*, Vol. 77, pgs. 5197–5200 (1980); (2) water-soluble carbodiimides for carboxyl to amino coupling, e.g. as disclosed by Hoare et al., *J. Biol. Chem.*, Vol. 242, pgs. 2447–2453 (1967); (3) bis-diazobenzidine (DBD) for tyrosine to tyrosine sidechain coupling, e.g. as disclosed by Bassiri et al., pgs. 46–47, in Jaffe and Behrman, eds. (cited above), and Walter et al. (cited above); and (4) maleimidobenzoyl-N-hydroxysuccinimide ester (MBS) for coupling cysteine (or other sulfhydryls) to amino groups, e.g. as disclosed by Kitagawa et al., *J. Biochem.* (Tokyo), Vol. 79, pgs. 233–239 (1976), and Lerner et al. (cited above).

A general rule for selecting an appropriate method for coupling a given peptide to a protein carrier can be stated as follows: the group involved in attachment should occur only once in the sequence, preferably at the appropriate end of the segment. For example, BDB should not be used if a tyrosine residue occurs in the main part of a sequence chosen for its potentially antigenic character. Similarly, centrally located lysines rule out the glutaraldehyde method, and the occurrences of aspartic and glutamic acids frequently exclude the carbodiimide approach. On the other hand, suitable residues can be positioned at either end of chosen sequence segment as attachment sites, whether or not they occur in the "native" protein sequence.

Internal segments, unlike the amino and carboxy termini, will differ significantly at the "unattached end" from the same sequence as it is found in the native protein where the polypeptide backbone is continuous. The problem can be remedied, to a degree, by acetylating the α-amino group and then attaching the peptide by way of its carboxy terminus.

The coupling efficiency to the carrier protein is conveniently measured by using a radioactively labeled peptide, prepared either by using a radioactive amino acid for one step of the synthesis or by labeling the completed peptide by the iodination of a tyrosine residue. The presence of tyrosine in the peptide also allows one to set up a sensitive radioimmune assay, if desirable. Therefore, tyrosine can be introduced as a terminal residue if it is not part of the peptide sequence defined by the native IL-4 polypeptide.

Preferred carriers are proteins, and preferred protein carriers include bovine serum albumin, myoglobulin, ovalbumin (OVA), keyhole limpet hemocyanin (KLH), or the like.

Peptides can be linked to KLH through cysteines by MBS as disclosed by Liu et al., *Biochemistry*, Vol. 18, pgs. 690–697 (1979). The peptides are dissolved in phosphate-buffered saline (pH 7.5), 0.1M sodium borate buffer (pH 9.0) or 1.0M sodium acetate buffer (pH 4.0). The pH for the dissolution of the peptide is chosen to optimize peptide solubility. The content of free cysteine for soluble peptides is determined by Ellman's method, Ellman, *Arch. Biochem. Biophys.*, Vol. 82, pg. 7077 (1959).

For each peptide, 4 mg KLH in 0.25 ml of 10 mM sodium phosphate buffer (pH 7.2) is reacted with 0.7 mg MBS (dissolved in dimethyl formamide) and stirred for 30 min at room temperature. The MBS is added dropwise to ensure that the local concentration of formamide is not too high, as KLH is insoluble in ≧30% formamide. The reaction product, KLH-MB, is then passed through Sephadex G-25 equilibrated with 50 mM sodium phosphate buffer (pH 6.0) to remove free MBS, KLH recovery from peak fractions of the column eluate (monitored by $OD_{280}$) is estimated to be approximately 80%.

KLH-MB is then reacted with 5 mg peptide dissolved in 1 ml of the chosen buffer. The pH is adjusted to 7–7.5 and the reaction is stirred for 3 hr at room temperature. Coupling efficiency is monitored with radioactive peptide by dialysis of a sample of the conjugate against phosphate-buffered saline, and ranged from 8% to 60%.

Once the peptide-carrier conjugate is available polyclonal or monoclonal antibodies are produced by standard techniques, e.g. as disclosed by Campbell *Monoclonal Antibody Technology* (Elsevier, N.Y., 1984); Hurrell, ed. *Monoclonal Hybridoma Antibodies: Techniques and Applications* (CRC Press, Boca Raton, Fla., 1982); Schreier et al. *Hybridoma Techniques* (Cold Spring Harbor Laboratory. New York, 1980); U.S. Pat. No. 4,562,003; or the like. In particular, U.S. Pat. No. 4,562,003 is incorporated by reference. For monoclonal antibody production, the first step is to immunize a host animal to obtain a source of B lymphocytes. The B lymphocytes are fused with an appropriate immortalizing cell line to form monoclonal antibody secreting hybridomas. Immortalizing cell lines are usually tumor cell lines, such as myelomas. Preferably, the host animals are rodents, and the immortalizing cell line is derived from rodent cells. More preferably they are from the same species. After formation, hybridomas are screened for those producing antibodies against the peptide of the invention. Immunization, lymphocyte harvesting, and cell fusion are all technique well known in the art. Roughly, immunization is carried out by a regimen of repeated injections into the host animal of the purified peptide-carrier conjugate, usually mixed with a suitable adjuvant. Immunization can be optimized by varying several factors, including the amount of antigen used for the primary injection and subsequent boosts, the route of injection, the time schedule for injecting and bleeding, and the use of adjuvant, e.g. Freund's complete or incomplete adjuvant. Techniques for fusion are also well known in the art, and in general, involve mixing the cells with a fusing agent such as, most commonly, polyethylene glycol.

Successful hybridoma formation is assessed and selected by standard procedures such as, for example, HAT selection. From among successful hybridomas, those successfully secreting the desired antibody are selected by assaying the culture medium for their presence. Ordinarily this is done using immunoreaction based assays, including, without limitation, Western blot, ELISA, or RIA assays. The antibodies can be recovered from the medium using standard protein purification techniques.

Both polyclonal and monoclonal antibodies can be screened by ELISA. As in other solid phase immunoassays, the test is based on the tendency of macromolecules to adsorb nonspecifically to plastic. The irreversibility of this reaction, without loss of immunological activity, allows the formation of antigen-antibody complexes with a simple separation of such complexes from unbound material.

To titrate antipeptide serum, peptide conjugated to a carrier different from that used in immunization is adsorbed to the wells of a 96-well microtiter plate. The adsorbed antigen is then allowed to react in the wells with dilutions of anti-peptide serum. Unbound antibody is washed away, and the remaining antigen-antibody complexes are allowed to react with antibody specific for the IgG of the immunized animal. This second antibody is conjugated to an enzyme such as alkaline phosphatase. A visible colored reaction product produced when the enzyme substrate is added indicates which wells have bound antipeptide antibodies. The use of spectrophotometer readings allows better quantification of the amount of peptide-specific antibody bound. High-titer antisera yield a linear titration curve between $10^{-3}$ and $10^{-5}$ dilutions.

EXAMPLES

The following examples serve to illustrate the present invention. Selection of particular peptides and/or carriers, and the choice of temperatures, concentrations, and the values of other variable parameters are only to exemplify application of the present invention and are not to be considered limitations thereof.

EXAMPLE I

Coupling peptide $Cys_3$—$Thr_{18}$ (CDITLQEIIKTLNSLT) to Ovalbumin and/or Myoglobulin and Production of Polyclonal Antibodies Thereto 50 mg of ovalbumin (OVA) and 50 mg of myoglobulin (MYO) (e.g. available from Sigma) were each dissolved in 10 ml of 0.1M sodium bicarbonate, and reacted with 1 ml of 0.12 iodoacetamide solution (88 mg of iodoacetamide dissolved in 4 ml 0.1M sodium bicarbonate) for 1 hour at room temperature in a 15 ml Falcon tube (Falcon Plastics, Oxnard, Calif.), or the like. Each reaction mixture was dialyzed overnight against 4 liters of 0.1M sodium bicarbonate at 4° C. Separately, 10 mg of CDITLQEIIKTLNSLT was dissolved in 2 ml of 0.1M DTT (dithiotheitol) solution (containing 50 mM Tris and 2.5 mM EDTA at pH8) in a 4 ml tube, incubated at 37° C. overnight; and then applied to a GF05 gel-filtration column (1.5×26.5 cm) (LKB, Bromma, Sweden) and eluted with a peptide elution buffer consisting of 0.015M acetic acid and 0.005M beta-mercaptoethanol. Three fractions of about 3.5 ml each which contained the reduced peptide were identified by optical density at 206 nm, collected, pooled, frozen in dry ice, and lyophilized overnight. Meanwhile OVA and MYO were recovered from dialysis, and clarified by filtration through 0.45 micrometer filters: OVA and MYO were activated by mixing each with 380 microliters of N-hydroxysuccinimide ester of iodoacetic acid (NHIA) (disclosed by Rector et al., in J. Immunol. Meth., Vol. 24, pg. 321 (1978)) dissolved in tetrahydrofuran (THF) (5 mg/ml); stirring for 30 minutes at room temperature, and dialyzing overnight against 4 liters PBS (1.8 g $NaH_2PO_4 \cdot H_2O$, 7.2 g $Na_2HPO_4 \cdot 7H_2O$; and 34 g NaCl in 4 liters $H_2O$). Separately the lyophilized peptide was resuspended in 5 ml of borate reduction buffer (2 g $Na_2B_4O_7 \cdot 10H_2O$, 17.4 g NaCl, and 336 mg $EDTA \cdot Na_2$ in liter $H_2O$ with pH adjusted to 8.5 with concentrated HCl, deoxygenated under nitrogen for 15 minutes, after which 178 mg ascorbate is added). The dialyzed iodoacetylated OVA and MYO were recovered, separately mixed with equal volumes (preferably 2 ml) of borate reduction buffer containing the peptide, and incubated overnight at room temperature. The resulting conjugates were analyzed by SDS-PAGE (12.5% gel). The conjugate containing solution was diluted with PBS to 1 mg/ml, sterile filtered, and aliquoted to convenient volumes (e.g. 500 microliters) for immunizations, and/or stored at 4° C.

Polyclonal anti-sera against the MYO conjugate was produced in both rats and rabbits (New Zealand White). The immunization schedule for rabbits is as follows: Initially (week 0) a 10 ml sample of serum was extracted as a control. One week later (week 1) 0.5 ml of peptide-carrier conjugate was mixed with 0.5 ml Freund's Complete Adjuvant and injected I.P. Three weeks later (week 4) a booster was given consisting of 0.5 ml peptide-carrier conjugate mixed with 0.5 ml Freund's Incomplete Adjuvant. The following week (week 5) an additional booster is given, again consisting of 0.5 ml peptide-carrier conjugate mixed with 0.5 ml Freund's Incomplete Adjuvant, followed by yet another identical booster the next week (week 6). On week 7 20 ml of serum was bled from the animal. After separating out the cellular fraction the serum indicated a positive anti-CDITLQEIIKTLNSLT titer by ELISA.

Rat immunization proceeded similarly except that the initial injection consisted of 0.15 ml PBS and 0.1 ml peptide-carrier conjugate mixed with 0.75 ml Freund's Complete Adjuvant, boosters consisted of 0.15 ml PBS and 0.1 ml peptide-carrier conjugate mixed with 0.75 ml Freund's Incomplete Adjuvant, and only 2-3 ml of serum was bled from the rat. Again, a positive anti-CDITLQEIIKTLNSLT reaction was detected by ELISA. The rat polyclonal anti-serum was also used in a Western blot analysis of elechophoretically separated recombinant human IL-4 produced by COS7 cells. The anti-serum was radioactively labeled using standard techniques, Swanstrom et al. Anal. Biochem., Vol. 86, pg. 184 (1978). The human recombinant IL-4 band was successfully identified by the antiserum.

EXAMPLE II

Coupling Peptide $Phe_{112}$—$Cys_{127}$ (FLERLKTIMREKYSKC) to Ovalbumin and/or Myoglobulin and Production of Polyclonal Antibodies Thereto.

Polyclonal antiserum against FLERLKTIMREKYSKC was produced in both a rabbit and a rat. Myoglobulin was the carrier, and essentially the same procedure was used for conjugation and immunization as described in Example I. The antisera both tested positive for anti-FLERLKTIMREKYSKC titer by ELISA. Both antisera could identify electrophoretically separated human recombinant IL-4 in Western blot analysis.

EXAMPLE III

Coupling Peptide $Asp_{31}$—$Cys_{46}$ (DIFAASKNTTEKETFC) to Myoglobulin and Production of Polyclonal Antibodies Thereto.

Polyclonal antiserum against DIFAASKNTTEKETFC coupled to myoglobulin was produced in a rat. The procedures described in Example I were employed. The antiserum was used to successfully detect electrophoretically separated human recombinant IL-4 in Western blot analysis.

EXAMPLE IV

Coupling Peptide $Leu_{52}$—$Cys_{65}$ (LRQFYSHHEKDTRC) to Myoglobulin and Production of Polyclonal Antibody Thereto.

Polyclonal antiserum against LRQFYSHHEKDTRC coupled to myoglobulin was produced in a rat using the same procedures as those described in Example I. The antiserum showed a positive anti-LRQFYSHHEKDTRC titer when tested by ELISA.

EXAMPLE V

Coupling Peptide $Lys_{61}$—$Phe_{82}$ (KDTRCLGATAQQFHRHKQLIRF) to Myoglobulin and Production of Polyclonal Antibodies Thereto.

Polyclonal antiserum against KDTRCLGATAQQFHRHKQLIRF coupled to myoglobulin was produced in a rat using the same procedures as those described in Example I. The antiserum showed a positive anti-KDTRCLGATAQQFHRHKQLIRF titer when tested by ELISA, but failed to identify electrophoretically separated human recombinant IL-4 by Western blot analysis.

EXAMPLE VI

Coupling Peptide $Leu_{83}$—$Lys_{102}$ (LKRLDRNLWGLAGLNSCPVK) to Myoglobulin and Production of Polyclonal Antibodies Thereto.

Polyclonal antiserum against LKRLDRNLWGLAGLNSCPVK coupled to myoglobulin was produced in a rat using the same procedures as those described in Example I. The antiserum showed a positive anti-LKRLDRNLWGLAGLNSCPVK titer when tested by ELISA.

EXAMPLE VII

Coupling Peptide $Cys_{99}$—$Asn_{111}$ (CPVKEANQSTLEN) to Myoglobulin and Production of Polyclonal Antibodies Thereto.

Polyclonal antiserum against CPVKEANQSTLEN coupled to myoglobulin was produced in a rat using the same procedures as those described in Example I. The antiserum showed a positive anti-CPVKEANQSTLEN titer when tested by ELISA, but failed to identify electrophoretically separated human recombinant IL-4 by Western blot analysis.

EXAMPLE VIII

Coupling of Peptide $Thr_{18}$—$Asp_{31}$ (TEQKTLCTELTVTD) to Myoglobulin and Production of Polyclonal Antibodies Thereto.

Polyclonal antiserum against TEQKTLCTELTVTD coupled to myoglobulin is produced in a rat using the same procedures as those described in Example I. The antiserum shows a positive anti-TEQKTLCTELTVTD titer when tested by ELISA.

The descriptions of the foregoing embodiments of the invention have been presented for purpose of illustration and description. They are not intended not be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A peptide consisting of 6–40 consecutive amino acids which are identical to the human interleukin-4 amino acid sequence [$His_1$—$Ser_{129}$] and which peptide further comprises relatively high average hydrophilicity and is capable of inducing the production of antibodies specific to IL-4 when conjugated to an immunogenic carrier and administered to the host.

2. The peptide of claim 1 selected from the group consisting of $His_1$—$Thr_6$, $His_1$—$Leu_7$, $His_1$—$Gln_8$, $His_1$—$Glu_9$, $His_1$—$Ile_{10}$, $His_1$—$Ile_{11}$, $His_1$—$Lys_{12}$, $His_1$—$Thr_{13}$, $His_1$—$Leu_{14}$, $His_1$—$Asn_{15}$, $His_1$—$Ser_{16}$, $His_1$—$Leu_{17}$, $His_1$—$Thr_{18}$, $His_1$—$Glu_{19}$, $His_1$—$Gln_{20}$, $His_1$—$Lys_{21}$, $His_1$—$Thr_{22}$, $His_1$—$Leu_{23}$, $His_1$—$Cys_{24}$, $His_1$—$Thr_{25}$, $His_1$—$Glu_{26}$, $His_1$—$Leu_{27}$, $His_1$—$Thr_{28}$, $His_1$—$Val_{29}$, and $His_1$—$Leu_{30}$.

3. The peptide of claim 1 selected from the group consisting of $Tyr_{124}$—$Ser_{129}$, $Lys_{123}$—$Ser_{129}$, $Glu_{122}$—$Ser_{129}$, $Arg_{121}$—$Ser_{129}$, $Met_{120}$—$Ser_{129}$, $Ile_{119}$—$Ser_{129}$, $Thr_{118}$—$Ser_{129}$, $Lys_{117}$—$Ser_{129}$, $Leu_{116}$—$Ser_{129}$, $Arg_{115}$—$Ser_{129}$, $Glu_{114}$—$Ser_{129}$, $Leu_{113}$—$Ser_{129}$, $Phe_{112}$—$Ser_{129}$, $Asn_{111}$—$Ser_{129}$, $Glu_{110}$—$Ser_{129}$, $Leu_{109}$—$Ser_{129}$, $Thr_{108}$—$Ser_{129}$, $Ser_{107}$—$Ser_{129}$, $Gln_{106}$—$Ser_{129}$, $Asn_{105}$—$Ser_{129}$, $Ala_{104}$—$Ser_{129}$, $Glu_{103}$—$Ser_{129}$, $Lys_{102}$—$Ser_{129}$, $Val_{101}$—$Ser_{129}$, $Pro_{100}$—$Ser_{129}$, and $Cys_{99}$—$Ser_{129}$.

4. A compound comprising a peptide of claim 1 conjugated to a carrier.

5. The compound of claim 4 comprising a peptide of claim 2 conjugated to a carrier selected from the group consisting of ovalbumin, myoglobulin, keyhole limpet hemocyanin, thyroglobulin, bovine serum albumin, and fibrinogen.

6. The compound of claim 4 comprising a peptide of claim 3 conjugated to a carrier selected from the group consisting of ovalbumin, myoglobulin, keyhole limpet hemocyanin, thyroglobulin, bovine serum albumin, and fibrinogen.

* * * * *